United States Patent
Leroux et al.

(10) Patent No.: US 6,338,859 B1
(45) Date of Patent: Jan. 15, 2002

(54) POLYMERIC MICELLE COMPOSITIONS

(75) Inventors: Jean-Christophe Leroux; Amina Souad Benahmed, both of Montreal (CA)

(73) Assignee: Labopharm Inc., Laval (CA)

( * ) Notice: Subject to any disclaimer, the term of this patent is extended or adjusted under 35 U.S.C. 154(b) by 0 days.

(21) Appl. No.: 09/606,398

(22) Filed: Jun. 29, 2000

(51) Int. Cl.$^7$ .......................... A61K 9/14; A61K 47/30; A61F 2/00
(52) U.S. Cl. ...................... 424/489; 424/426; 514/772.3
(58) Field of Search ................... 424/426, 425, 424/78.08, 78.18, 489, 486; 514/712.3; 530/322

(56) References Cited

U.S. PATENT DOCUMENTS

| | | | | |
|---|---|---|---|---|
| 5,693,751 A | * | 12/1997 | Sakurai et al. | 530/322 |
| 5,702,717 A | * | 12/1997 | Cha et al. | 424/425 |

OTHER PUBLICATIONS

Allen et al., 2000, "Polycaprolactone–b–poly(ethylene oxide) copolymer micelles as a delivery vehicle for dihydrotestosterone", J. Controlled Release 63:275–286.

Allen et al., 1999, "Nano–engineering block copolymer aggregates for drug delivery", iColloids and Surfaces B: Biointerfaces 16:3–27.

Bader et al., 1984, "Watersoluble polymers in medicine", Die Angew. Makromolekulare Chemie 123/124:457–485.

Cao et al., 1991, "Fluorescence studies of amphiphilic poly(methacrylic acid)–block–polystyrene–block– poly(methacrylic acid) micelles", Macromolecules 24:6300–6305.

Chung et al., 2000, "Inner core segment design for drug delivery control of thermo–responsive polymeric micelles", J. Controlled Release 65:93–103.

De Jaeghere et al., 1999, "Formulation and lyoprotection of poly(lactic acid–co–ethylene oxide) nanoparticles: influence on physical stability and in vitro cell uptake", Pharm. Res. 16:859–866.

Eguiburu et al., 1996, "Graft copolymers for biomedical applications prepared by free radical polymerization of poly(L–lactide) macromonomers with vinyl and acrylic monomers", Polymer 37:3615–3622.

Franks et al., 1977, "Polymeric cryoprotectants in the preservation of biological ultrastructure", J. Microscopy 110:223–238.

Gabaston et al., 1998, "Living free–radical dispersion polymerization of styrene", Macromolecules 31:2883–2888.

Inoue et al., 1998, "An AB block copolymer of oligo(methyl methacrylate) and poly(acrylic acid), for micellar delivery of hydrophobic drugs", J. Controlled Release 51:221–229.

Jones and Leroux, 1999, "Polymeric micelles—a new generation of colloidal drug carriers", Eur. J. Pharmaceut. Biopharmaceut. 48:101–111.

Kabanov et al., 1989, "The neuroleptic activity of haloperidol increases after its solubilization in surfactant micelles", FEBS Lett. 258:343–345.

Kamada et al., 1999, "Molecular design of conjugated tumor necrosis factor–α:synthesis and characteristics of polyvinyl pyrrolidone modified tumor necrosis factor–α", Biochem. Biophys. Res. Comm. 257:448–453.

Kataoka et al., 2000, "Doxorubicin–loaded poly(ethylene glycol)–poly(β–benzyl–L–aspartate) copolymer micelles: their pharmaceutical characteristics and biological significance", J. Controlled Release 64:143–153.

Kim and Kim, 1999, "Thermo–sensitive self–aggregates prepared from cholic acid–conjugated amine–terminated poly(N–isopropylacrylamide) for drug delivery", Proc. Intl. Symp. Control. Rel. Bioact. Mater. 26:#6219.

Molyneux, 1983, "The physical chemistry and pharmaceutical applications of polyvinylpyrrolidone", Proc. Intl. Symp. on Povodine, Lexington, KY, Apr. 17–20, 1983, pp. 1–19.

Poujol et al., 2000, "Molecular microencapsulation: paclitaxel formations in aqueous medium using hydrophobized poly(L–lysine citramide imide)", J. Bioactive and Compatible Polymers 15:99–114.

Rutt et al., 1994, "Ion–free latex films as dual–phase electrolytes: styrene–butadiene rubber and nitrile–butadiene rubber synthesized by emulsion polymerization with poly(vinyl pyrrolidone) stabilizer", J. Polymer Sci. 32:2505–2515.

Scholz et al., 1995, "A novel reactive polymeric micelle with aldehyde groups on its surface", Macromolecules 28:7295–7297.

Torchilin, 1998, "Polymer–coated long–circulating microparticulate pharmaceuticals", J. Microencapsulation 15:1–19.

Townsend and DeLuca, 1988, "Use of lyoprotectants in the freeze–drying of a model protein, ribonuclease A", J. Parenteral Sci. Technol. 42:190–199.

Yokoyama et al., 1998, "Incorporation of water–insoluble anticancer drug into polymeric micelles and control of their particle size", J. Controlled Release 55:219–229.

Zhang, 1996, "Development of amphiphilic diblock copolymers as micellar carriers of taxol", Intl. J. Pharmaceut. 132:195–206.

Zhang and Eisenberg, 1995, "Multiple morphologies of "crew–cut" aggregates of polystyrene–b–poly(acrylic acid) block copolymers", Science 268:1728–1731.

Zhao et al., 1990, "Fluorescence probe techniques used to study micelle formation in water–soluble block copolymers", Langmuir 6:514–516.

Kwon et al., "Polymeric Micelles as New Drug Carriers" Advanced Drug Delivery Rev., vol. 21 pp. 107–116 (1996).*

* cited by examiner

*Primary Examiner*—Thurman K. Page
*Assistant Examiner*—Blessing Fubara
(74) *Attorney, Agent, or Firm*—Pennie & Edmond LLP

(57) ABSTRACT

Novel polymeric micelles which are used to deliver therapeutic agents, including anti tumor drugs.

15 Claims, No Drawings

POLYMERIC MICELLE COMPOSITIONS

1. FIELD OF THE INVENTION

The present invention relates to compositions comprising polymeric micelles which are useful for delivery of therapeutic agents, including, but not limited to, anticancer drugs.

2. BACKGROUND OF THE INVENTION

A major obstacle associated with the use of chemotherapeutic agents is the lack of selectivity toward cancerous cells. This lack of selectivity has been linked to the toxic side effects of the use of such agents due to their delivery to both normal and abnormal cells. Lack of selectivity of drugs towards target cells is also a problem in the treatment of a variety of disorders in addition to cancer. Much research effort has focused on development of carriers for drugs that can selectively deliver the drug to target cells. For example, in order to improve the specific delivery of drugs with a low therapeutic index, several drug carriers such as liposomes, microparticles, nano-associates and drug-polymer conjugates have been studied.

Of the targeting devices studied liposomes (phospholipid vesicles) have attracted considerable attention. Their targeting efficacy is, however, limited by quick scavenging by reticuloendothelial (RE) cells of the liver and spleen, instability in the plasma, limited capability at extravasation due to size, technical problems with their production and susceptibility to oxidation. Solutions to individual problems have been found, but solutions to more than one problem have rarely been combined in a single composition. For example, if recognition by RE cells is reduced and stability improved, it is difficult to obtain stable liposomes having a diameter of less than 50 nm.

Polymeric micelles were first proposed as drug carriers by Bader, H. et al. in 1984. Angew. Makromol. Chem. 123/124 (1984) 457–485. Polymeric micelles have been the object of growing scientific attention, and have emerged as a potential carrier for drugs having poor water solubility because they can solubilize those drugs in their inner core and they offer attractive characteristics such as a generally small size (<100 nm) and a propensity to evade scavenging by the reticuloendothelial system (RES).

Micelles are often compared to naturally occurring carriers such as viruses or lipoproteins. All three of these carriers demonstrate a similar core-shell structure that allows for their contents to be protected during transportation to the target cell, whether it is DNA for viruses or water-insoluble drugs for lipoproteins and micelles.

Lipoproteins were proposed as a vehicle for the targeting of antitumor compounds to cancer cells because tumors express an enhanced need for low density lipoproteins. The efficiency of lipoproteins as carriers has been questioned, however, mainly because drug-incorporated lipoproteins would also be recognized by healthy cells and because they would have to compete with natural lipoproteins for receptor sites on tumors. Conversely, viral carriers are mainly used for the delivery of genetic material and may have optimal use in applications that do not require repeated application of the delivery vehicle, since they are likely to elicit an immune response.

Polymeric micelles seem to be one of the most advantageous carriers for the delivery of water-insoluble drugs. Polymeric micelles are characterized by a core-shell structure. Pharmaceutical research on polymeric micelles has been mainly focused on copolymers having an A-B diblock structure with A, the hydrophilic shell moieties and B the hydrophobic core polymers, respectively. Multiblock copolymers such as poly(ethylene oxide)-poly(propylene oxide)- poly(ethylene oxide) (PEO-PPO-PEO) (A-B-A) can also self-organize into micelles, and have been described as potential drug carriers. Kabanov, A.V. et al., FEBS Lett. 258 (1989) 343–345. The hydrophobic core which generally consists of a biodegradable polymer such as a poly(β-benzyl-L-aspartate) (PBLA), poly (DL-lactic acid) (PDLLA) or poly (ε-caprolactone) (PCL), serves as a reservoir for an insoluble drug, protecting it from contact with the aqueous environment. The core may also consist of a water-soluble polymer, such as poly(aspartic acid) (P(Asp)), which is rendered hydrophobic by the chemical conjugation of a hydrophobic drug, or is formed through the association of two oppositely charged polyions (polyion complex micelles). Several studies describe the use of non- or poorly biodegradable polymers such as polystyrene (Pst) or poly (methyl methacrylate) (PMMA) as constituents of the inner core. See, e.g., Zhao, C. L. et al., Langmuir 6 (1990) 514–516; Zhang, L. et al., Science 268 (1995) 1728–1731 and Inoue, T. et al., J. Controlled Release 51 (1998) 221–229. In order to be considered as clinically relevant drug carriers, non-biodegradable polymers must be non-toxic and have a molecular weight sufficiently low to be excreted via the renal route. The hydrophobic inner core can also consist of a highly hydrophobic small chain such as an alkyl chain or a diacyllipid such as distearoyl phosphatidyl ethanolamine (DSPE). The hydrophobic chain can be either attached to one end of a polymer, or randomly distributed within the polymeric structure.

The shell is responsible for micelle stabilization and interactions with plasmatic proteins and cell membranes. It usually consists of chains of hydrophilic, non-biodegradable, biocompatible polymers such as PEO. The biodistribution of the carrier is mainly dictated by the nature of the hydrophilic shell. Other polymers such as poly(N-isopropylacrylamide) (PNIPA) and poly(alkylacrylic acid) impart temperature or pH sensitivity to the micelles, and could eventually be used to confer bioadhesive properties. Micelles presenting functional groups at their surface for conjugation with a targeting moiety are also known. See, e.g., Scholz, C. et al., Macromolecules 28 (1995) 7295–7297.

Poly(N-vinyl-2-pyrrolidone) (PVP) is a well-known water-soluble, biocompatible, amphiphilic polymer with the highly polar lactam group surrounded by apolar methylene groups in the backbone and methine a group in the ring. PVP is conventionally used as a steric stabilizer for the synthesis of polystyrene latexes. See, e.g., Gabaston, L. I. et al., Macromolecules 31 (1998) 2883–2888; Rutt, J. S. et al., J. Polym. Sci.: Part A: Polym. Chem., 32 (1994) 2505–2515. PVP may be also used as a cryoprotectant and a lyoprotectant. See, e.g. Skaer, H. B. et al., J. Microsc. 110 (1977) 257–270; Townsend, M. W. et al., J. Parenter. Sci. Technol., 42 (1988) 190–199.

In comparison with PEG, PVP is remarkable for the diversity of interactions it shows towards non-ionic and ionic cosolutes. See, Molyneux, P., Proc. Int. Symp. Povidone (1983) 1–19. Binding takes place most markedly with molecules having long alkyl chains or aromatic moieties. Similarly to PEG, PVP can also increase the in vivo circulation time of colloidal carriers and peptides/proteins. See, e.g., Kamada, H. et al., Biochem. Biophys. Res. Commun. 257 (1999) 448–453; Torchilin, V. P., J. Microencapsulation 15 (1998) 1–19. Further it has also been shown that nanoparticles containing diblock copolymers of poly(D,L-lactic acid) and poly (ethylene glycol) (PEG) aggregate after freeze drying. See, De Jaeghere, F. et al., Pharm. Res. 16 (1999) 859–866. This problem was circumvented by the use of a lyoprotectant. This problem would be obviated by use of PVP since the PVP is itself a lyoprotectant.

N-vinyl pyrrolidone (VP) can be copolymerized with a wide variety of vinyl monomers. With electronegative monomers, it forms alternating copolymers, whereas with acrylates, it forms random copolymers. For instance, a graft copolymer composed of poly(L-lactide) (PLLA) and PVP Has been prepared. See, Eguiburu, J. L., et al., J. San Roman, Polymer 37 (1996) 3615–3622. In this study, a PLLA macromonomer was copolymerized with VP, but the formation of polymeric micelles was not assessed.

Until now, most studies dealing with the preparation of biodegradable polymeric micelles have been focused on the utilization of PEG for the formation of the hydrophilic shell. See, e.g., X. Zhang, X., et al., Inter. J. Pharm. 132 (1996) 195–206; Yokoyama,M., et al., J. Control. Release 55 (1998) 219–229 and Allen, C., et al., J. Control. Release 63(2000) 275–286.

Therefore, there remains a need for new biocompatible-biodegradable polymeric micellar systems which do not contain PEG, but which would exhibit good solubilization properties and provide several binding sites to a variety of drugs. They should also be readily redispersed or redissolved following the addition of water to the freeze-dried form. The present invention such a system composed of diblock PVP-Poly(D,L-lactide) (PDLLA).

3. SUMMARY OF THE INVENTION

The present invention provides a micelle-forming composition, comprising:

a hydrophobic core surrounded by a hydrophilic shell, and wherein said hydrophilic shell is PVP.

The present invention further provides a micelle-forming composition, comprising:

a therapeutic agent; and a hydrophobic core surrounded by a hydrophilic shell, and wherein said hydrophilic shell is PVP, and wherein said therapeutic agent is contained within said micelle.

The present invention further provides methods for loading the polymeric micelles with at least one suitable therapeutic agent.

The present invention also provides a polymeric micelle composition, comprising a therapeutic agent, wherein the therapeutic agent can be protected from chemical interactions, such as hydrolysis, by being contained within the hydrophobic core or hydrophilic shell of said micelle.

These and other features and advantages of the invention will be more readily understood by those of ordinary skill in the art from a reading of the following detailed description.

4. DETAILED DESCRIPTION OF THE INVENTION

The present invention provides a colloidal composition consisting of polymeric micelles which may be used to deliver therapeutic agents which have poor water solubility and/or a specific affinity for the hydrophilic shell. The polymeric micelles are characterized by a core shell structure, wherein a hydrophobic core is surrounded by a hydrophilic shell. The hydrophilic shell comprises a hydrophilic polymer or copolymer.

The hydrophilic polymer of the present invention is a polymer or copolymer of poly(N-vinyl-2-pyrrolidone) (PVP).

The hydrophobic moiety constitutes the core of the micelle. The hydrophobic moiety may be chosen from polyesters, such as poly(glycolic acid), poly(lactic acid), poly(D-lactic acid), poly(D,L-lactic acid), lactide/glycolide copolymers, polycaprolactone and derivatives thereof; poly) orthoesters and derivatives thereof; polyanhydrides and derivatives thereof; tyrosine derived pseudo-poly(amino acids) and derivatives thereof; polyphosphazenes and derivatives thereof; poly(alkylacrylate) and derivatives thereof; poly(β-benzyl-L-aspartate) and derivatives thereof and combinations thereof. A preferred hydrophobic moiety is of poly(D,L-lactide (PDLLA). The PDLLA is present at a concentration varying between about 10% and about 50% (w/w).

4.1 Formation of Micelles

Micelle formation occurs as a result of two forces. One is an attractive force that leads to the association of molecules, while the other is a repulsive force that prevents unlimited growth of the micelles to a distinct macroscopic phase. Amphiphilic copolymers self-associate when placed in a solvent that is selective for either the hydrophilic or hydrophobic polymer.

The micellization process of amphiphilic copolymers is similar to that for low molecular weight surfactants. At very low concentrations, the polymers exist only as single chains. As the concentration increases to reach a critical value called the critical association concentration ("CAC"), polymer chains start to associate to form micelles in such a way that the hydrophobic part of the copolymer will avoid contact with the aqueous media in which the polymer is diluted. At the CAC, an important quantity of solvent can be found inside the micellar core, and micelles are described as loose aggregates which exhibit larger size than micelles formed at higher concentrations. At those concentrations, the equilibrium will favor micelle formation, micelles will adopt their low energy state configuration and the remaining solvent will be gradually released from the hydrophobic core resulting in a decrease in micellar size. Amphiphilic copolymers usually exhibit a CAC which is much lower than that of low molecular weight surfactants. For example, the CAC of PEO-PBLA and PNIPA-PSt are between 0.0005–0.002%. Some amphiphilic copolymers, however, exhibit much higher CAC, reaching up to 0.01–10% in the case of poloxamers. Amphiphilic copolymers with high CAC may not be suitable as drug targeting devices since they are unstable in an aqueous environment and are easily dissociated upon dilution.

The micellization of amphiphilic copolymers can result in two different types of micelles depending on whether the hydrophobic chain is randomly bound to the hydrophilic polymer or grafted to one end of the hydrophilic chain. Micelles formed from randomly modified polymers are generally smaller than end-modified polymers. The micellar size is mainly determined by the hydrophobic forces which sequester the hydrophobic chains in the core, and by the excluded volume repulsion between the chains which limits their size. The difference in the balance of these two forces in random and end-modified copolymers may account for their different size. When terminal hydrophobic groups associate to form micelles, the water clusters immobilized around the hydrophobic segments are excluded from the core and no direct interaction exists between the core and the hydrophilic shell, which remains as mobile linear chains in the micellar structure. Randomly modified polymers, however, associate in such a manner that the hydrophobic and hydrophilic parts of the polymer are entangled together allowing possible contact between the core and the aqueous medium. This is an important issue, since exposed hydrophobic cores may result in secondary aggregation of polymeric micelles. Secondary aggregation has also been proposed as an hypothesis to explain the presence of large particles (>100 nm) in micellar systems of PEO-P(Asp) bearing conjugated doxorubicin (DOX).

4.2 Determination of Critical Association Concentration (CAC)

Light scattering is widely used for the determination of the molecular weight and aggregation number of micelles. The onset of micellization can, however, be detected only if the CAC falls within the sensitivity of the scattering method. This is rarely the case for polymers in water. Gel permeation chromatography (GPC) under aqueous conditions can be employed since single chains and micellar fractions of copolymers exhibit different elution volumes. It is also possible to simultaneously determine by GPC the molecular weight of the micelles and their aggregation number. It is important that the integrity of polymeric micelles be maintained during their elution through the size exclusion column. Adsorption of the polymer on the column may also present a problem, especially at concentrations close to the CAC where micelles consist of large loose aggregates.

A preferred method to determine the CAC involves the use of fluorescent probes, among which pyrene is widely used. Pyrene is a condensed aromatic hydrocarbon that is highly hydrophobic and sensitive to the polarity of the surrounding environment. Below the CAC, pyrene is solubilized in water, a medium of high polarity. When micelles are formed, pyrene partitions preferentially toward the hydrophobic domain afforded by the micellar core, and thus experiences a non-polar environment. Consequently, numerous changes such as an increase in the fluorescence intensity, a change in the vibrational fine structure of the emission spectra, and a red shift of the (0,0) band in the excitation spectra are observed. The apparent CAC can be obtained from the plot of the fluorescence of pyrene, the $I_1/I_3$ ratio from emission spectra or the $I_{338}/I_{333}$ ratio from the excitation spectra versus concentration. A major change in the slope indicates the onset of micellization. The $I_1/I_3$ ratio is the intensity ratio between the first and third highest energy emission peaks and is measured at a constant excitation wavelength and variable emission wavelengths corresponding to $I_1$ and $I_3$. The CAC determined with fluorescence techniques needs to be carefully interpreted for two reasons. First, the concentration of pyrene should be kept extremely low ($10^{31\ 7}$ M), so that a change in slope can be precisely detected as micellization occurs. Second, a gradual change in the fluorescence spectrum can sometimes be attributed to the presence of hydrophobic impurities or association of the probe with individual polymeric chains or premicellar aggregates. Changes in anisotropy of fluorescent probes have also been associated with the onset of micellization.

Polymeric micelles such as those of the compositions of the invention are characterized by their small size (10–100 nm). Besides being needed for extravasation of the carrier materials, this small size permits the sterilization of the composition to be effected simply by filtration, and minimizes the risks of embolism in capillaries. This is not the situation encountered with larger drug carriers. Micellar size depends on several factors including copolymer molecular weight, relative proportion of hydrophilic and hydrophobic chains and aggregation number. The size of micelles prepared by dialysis can be affected by the organic solvent used to dissolve the polymer.

Micellar diameter and size polydispersity can be obtained directly in water or in an isotonic buffer by dynamic light scattering (DLS). DLS can also provide information on the sphericity of polymeric micelles.

Micellar size can also be estimated by methods such as atomic force microscopy (AFM), transmission electron microscopy (TEM) and scanning electron microscopy (SEM). These methods allow the characterization of the micelle shape and size dispersity. Ultracentrifugation velocity studies are sometimes performed to assess the polydispersity of polymeric micelles.

4.3 Incorporation of Therapeutic Agents into Polymeric Micelles

Loading of a therapeutic agent into the micelles can be realized according to techniques well known to one skilled in the art. For example, loading may be effected by dissolution of the compound in a solution containing preformed micelles, by the oil-in-water procedure or the dialysis method.

Therapeutic agents which may be used are any compounds, including the ones listed below, which can be entrapped, in a stable manner, in polymeric micelles and administered at a therapeutically effective dose. Preferably, the therapeutic agents used in accordance with the invention are hydrophobic in order to be efficiently loaded into the micelles. However it may be possible to form stable complexes between ionic micelles and oppositely charged hydrophilic compounds such as antisense oligonucleotides. Suitable drugs include antitumor compounds such as phthalocyanines (e.g. aluminum chloride phthalocyanine), anthracyclines (e.g. doxorubicin (DOX)), poorly soluble antimetabolites (e.g. methotrexate, mitomycin, 5-fluorouracil) and alkylating agents (e.g. carmustine). Micelles may also contain taxanes such as paclitaxel.

Additional drugs which can be contained in micelles are conventional hydrophobic antibiotics and antifungal agents such as amphotericin B, poorly water soluble immunomodulators such as cyclosporin, poorly water soluble antiviral drugs such as HIV protease inhibitors and poorly water-soluble steroidal (e.g. dexamethasone), non-steroidal (e.g. indomethacin) anti-inflammatory drugs and genome fragments.

Further, drugs can be incorporated into the polymeric micelle compositions of the invention by means of chemical conjugation or by physical entrapment through dialysis, emulsification techniques, simple equilibration of the drug and micelles in an aqueous medium or solubilization of a drug/polymer solid dispersion in water.

Hydrophilic compounds such as proteins may also be incorporated in the polymeric micelle compositions of the invention. The incorporation of such hydrophilic species may, however, require the chemical hydrophobization of the molecule or a particular affinity for the hydrophilic shell. Polyionic compounds can be incorporated through the formation of polyionic complex micelles.

Physical entrapment of drugs is generally carried out by a dialysis or oil-in-water emulsion procedure. The dialysis method consists in bringing the drug and copolymer from a solvent in which they are both soluble, such as ethanol or N,N-dimethylformamide, to a solvent that is selective only for the hydrophilic part of the polymer, such as water. As the good solvent is replaced by the selective one, the hydrophobic portion of the polymer associates to form the micellar core incorporating the insoluble drug during the process. Complete removal of the organic solvent may be brought about by extending the dialysis over several days. In the oil-in-water emulsion method, a solution of the drug in a water-insoluble volatile solvent, such as chloroform, is added to an aqueous solution of the copolymer to form an oil-in-water emulsion. The micelle-drug conjugate is formed as the solvent evaporates. The main advantage of the dialysis procedure over the latter method is that the use of potentially toxic solvents such as chlorinated solvents can be avoided.

The drug loading procedure may affect the distribution of a drug within the micelle. For example, Cao et al. (Macromolecules 24 (1991) 6300–6305), showed that pyrene incorporated in micelles as they were forming was not protected from the aqueous environment as well as pyrene incorporated after micelles were formed, although the first method yielded a drug loading three times higher than the second method.

Entrapment efficiency of the polymeric micelles of the invention depends on the initial amount of drug added. Exceeding the maximum loading capacity results in precipitation of the therapeutic agent, and consequently, lower yield. Further, efficiency of loading of the therapeutic agent depends on the aggregation number of copolymer. Micelles showing a higher aggregation number allow a greater amount of drug to be solubilized in their inner core.

4.4 Examples of Therapeutic Agent-Loaded Polymeric Micelles

Examples of compounds loaded into polymeric micelles as well as the corresponding drug loading procedure are given in table 1. The polymeric micelle compositions of the invention are believed to be suitable for use as delivery systems for a wide range of therapeutic agents, including, but not limited to, anticancer drugs, plasmid DNA, antisense oligonucleotides or for the delivery of diagnostic agents to a specific organ in the body.

TABLE 1

Examples of drugs and tracers loaded into polymeric micelles

| Drug | Polymer | Incorporation Mode | Micelle size with drug (nm) |
|---|---|---|---|
| Amphotericin B | PEO-PBLA | P | 26 |
| Antisense oligonucleotide | PEO-P(Lys) | EA | 50 |
| Cisplatin | PEO-P(Asp) | C | 16 |
| Cyclophosphamide | PEO-P(Lys) | C | n.a. |
| Dequalinium | PEO-PE | P | 15 |
| Doxirubicin (DOX) | PEO-P(Asp) | C | 50 |
| DOX | PEO-P(Asp) | C | 14–131 |
| DOX | PEO-P(Asp) | C | 17–42 |
| DOX | PEO-PBLA | P | 30 |
| DOX | PEO-PDLLA | P | n.a. |
| DOX | PEO-PBLA | P | 37 |
| DOX | PEO-P(Asp) | P + C | n.a. |
| DOX | PNIPA-PBMA | P | n.a. |
| DOX | PAA-PMMA | P | n.a. |
| Gd-DTPA-PE $^{111}$In-DTPA-SA | PEO-PE | P | 20 |
| Haloperidol | PEO-PPO-PEO | P | n.a. |
| Haloperidol | PEO-PPO-PEO | P | 15 |
| Indomethacin | PEO-PBLA | P | 25–29 |
| Indomethacin | PEO-PCL | P | 145–165 |
| Indomethacin | PEO-PCL | P | 114–156 |
| Iodine derivative of benzoic acid | PEO-P(Lys) | C | 80 |
| KRN-5500 | PEO-PBLA | P | |
| | PEO-(C$_{16}$, BLA) | | 71* |
| | PEO-P(Asp, BLA) | | |
| Paclitaxel | PEO-PDLLA | P | n.a. |
| Paclitaxel | LCC | P | <100 |
| Plasmid DNA | PEO-P(Lys) | EA | 140–150 |
| Soybean trypsin inhibitor | PEO-PE | P | 15 |
| Testosterone | PEO-PDLLA | P | n.a. |
| Topoisomerase II inhibitor ellipticine | PEO-PE | P | n.a. | n.a.: not available, P: physical entrapment, C: chemical bonding, EA: electrostatic association
*After the sonication of PEO(C$_{16}$, BLA) aggregates Evidence of drug incorporation can be obtained by GPC or DLS since both methods detect changes in micellar size. The presence of drugs is usually associated with such an increase in the size of micelles. The location of a drug inside the micelle core may be demonstrated by quenching experiments. For instance, iodide (I) which is a water soluble quencher of DOX, does not affect the fluorescence of the micelle-incorporated drug but quenches the fluorescence of the free drug. Such experiments showed that DOX was retained in PEO-PBLA after freeze drying and reconstitution in water. In the case of DOX, the self-association of the drug in the micelle core also results in a decrease in the fluorescence intensity of the drug. Recently, the retention and slow release of amphotericin B from polymeric micelles was indirectly ascertained by measuring the decrease of its hemolytic activity after incorporation into PEO-PBLA micelles.

4.5 Pharmaceutical Applications

The polymeric micelle compositions of the invention are suitable for use in a variety of pharmaceutical fields, such as oral delivery, sustained release and site-specific drug targeting. Preferably, the micelles of the invention are used as a transport for water-insoluble drugs.

5. EXAMPLES

The following example is illustrative, and is not intended to limit the scope of the present invention.

Materials

Commercial solvents were purchased from Moquin Scientific (Terrebonne, Quebec) and reagents from Aldrich (Milwaukee, Wis.). N-vinyl-2-pyrrolididone (VP), 2-isopropoxyethanol, potassium hydride (KH) 35 wt. % in mineral oil and 18-crown-6 were used without further purification. D,L-lactide was recrystallized three times from anhydrous ethyl acetate at 60° C. and then dried at room temperature for 24 h under reduced pressure over $P_2O_5$. Tetrahydrofuran (THF) was refluxed and distilled over sodium and benzophenone under a dry argon atmosphere just before use. 1,1'-Azobis (cyclohexane-carbonitrile) (ACCN) was purified by precipitation into water from an ethanol solution and dried under vacuum for 4 days. Sepharose 2B was obtained from Sigma (Saint Louis, Mo.) and equilibrated with water before use. The dialysis bags used in the micelle preparation were Spectra/Por Membranes (Rancho Dominguez, Calif.), MWCO 6000–8000. All reactions were carried out in round-bottom flasks which had been previously flamed, and which were fitted with a rubber septum under a dry argon atmosphere.

Molecular weights were determined by gel permeation chromatography (GPC, Waters Model 600, Milford, MA) with a Millenium software program. Three Styragel columns (Waters, HR1, HR3, HR4, 4.6×300 mm) and differential refractometer detector (Waters 2410) were used. The mobile phase was CHCl$_3$ (30° C. and 1 mL /min). Column calibration was performed with polystyrene standards (Aldrich, Milwaukee, Wis.). $^1$H and $^{13}$C NMR spectra were recorded on Varian 300 and Brucker AMX 600 spectrometers in deuterated chloroform, respectively.

The critical association concentration (CAC) was determined by a steady-state pyrene fluorescence method. It has been previously shown that with increasing concentrations of amphiphilic polymers in an aqueous solution of pyrene, there is a shift of the (0,0) band from 333 to 338.5 nm in the excitation spectra of pyrene. This change, as measured by the $I_{338}/I_{333}$ intensity ratio, accompanies the transfer of pyrene molecules from a water environment to the hydrophobic micellar cores and can be used to estimate the apparent CAC. Several polymeric solutions in water differing in polymer concentration but each containing $10^{31\ 7}$ M of pyrene were prepared and kept stirred overnight in the dark at 4° C. Steady-state fluorescent spectra were measured ($\lambda_{em}$=390 nm) after 5 min under stirring at 20° C. using a Serie 2 Aminco Bowman fluorimeter (Spectronics Instruments Inc., Rochester, N.Y.). Micelle size was determined in water and PBS at 20° C. by dynamic laser scattering (DLS) using unimodal and differential size distribution processor (SDP) intensity analysis (N4Plus, Coulter Electronics, Hialeah, Fla.).

Preparation of PVP-OH

Hydroxy-terminated PVP (PVP-OH) was prepared by radical polymerization using 2-isopropoxyethanol as a chain transfer agent. VP (5 mL, 47 mmol) and ACCN (0.11 g, 0.45 mmol) were solubilized in 60–300 mL 2-isopropoxyethanol. These solutions were degassed with argon. Polymerization was carried out at 80° C. with stirring under a dry argon atmosphere for 24 h. After evaporation of 2-isopropoxyethanol, the polymer was precipitated in an excess of diethyl ether. The white powder so obtained was purified three times by solubilization in the minimum amount of $CH_2Cl_2$ and reprecipitated from diethyl ether and finally dried in vacuum.

Characterization of PVP-OH $^1$H NMR $\delta$(ppm): 1.15 (m, $CH_3$), 3.5–4 (broad signal, C$\underline{H}$PVP) $^{13}$C NMR $\delta$(ppm): 175 (C=O PVP), 63.05 ($\underline{C}H_2OH$)

adding 1 mL acetic acid and 5 mL of water. The polymer solution was dialyzed against water for 24 h at 4° C. to form micelles. After dialysis, the solution was centrifuged for 30 min at 40790×g to remove any poly(D,L-lactide) (PDLLA) homopolymer. The supernatant was frozen and lyophilized in a freeze dry system (Labconco, model 77535, Kansas City, Mo.). The freeze-dried powder was resolubilized in water and free PVP-OH was removed by passage over a Sepharose 2B column (Pharmacia, 1×40 cm). The micellar solution was frozen, lyophilized for 2 days and stored at −20° C. until use.

Characterization of PVP-PDLLA $^1$H NMR $\delta$(ppm) : 5.2 (m, C$\underline{H}$PDLLA) , 3.5-4 (broad signal, C$\underline{H}$PVP) $^{13}$C NMR $\delta$(ppm): 175 (C=O PVP), 169 (C=O PDLLA), 69.8 ($\underline{C}H$—$CH_3$ PDLLA), 17.2 (CH—$\underline{C}H_3$ PDLLA).

TABLE 2

Characterization of PVP-PDLLA and polymeric micelles

| PVP-OH Batch # | PVP-PLA Batch # | PVP:PLA (wt. %)[a] | $M_w$ | $M_n$ | $M_w/M_n$ | Micelle size[b] in water (nm) | Micelle size[b] in PBS (nm) | CAC (mg/L) |
|---|---|---|---|---|---|---|---|---|
| 1 | 1a | 59:41 | 15151 | 7955 | 1.9 | 56 ± 24 | 44 ± 21 | 10.2 |
| 2 | 2a | 74:26 | 8500 | 5500 | 1.5 | 54 ± 24 | 59 ± 25 | 3.4 |
| 3 | 3a | 60:40 | 8985 | 6576 | 1.3 | 106 ± 45 | 95 ± 37 | 2 |
| 3 | 3b | 33:67 | 14500 | 12084 | 1.2 | 168 ± 71 | 160 ± 64 | 2.6 |
| 3 | 3c | 88:12 | 6700 | 4500 | 1.4 | 74 ± 31 | 92 ± 41 | 22.4 |
| 4 | 4a | 60:40 | 7134 | 5488 | 1.3 | 51 ± 22 | 48 ± 19 | 1.9 |
| 4 | 4b | 64:36 | 7920 | 5100 | 1.5 | 50 ± 22 | 68 ± 31 | 2.5 |
| 5 | 5a | 65:35 | 5737 | 3685 | 1.5 | 48 ± 21 | 58 ± 23 | 4.3 |

[a]determined by GPC
[b]from unimodal analysis

TABLE 1

PVP average molecular weights

| PVP-OH Batch # | Solvent/VP (volume ratio) | $M_w$ | $M_n$ | $M_w/M_n$ |
|---|---|---|---|---|
| 1 | 12 | 8516 | 4731 | 1.8 |
| 2 | 30 | 5726 | 4090 | 1.4 |
| 3 | 30 | 7163 | 3964 | 1.8 |
| 4 | 40 | 5900 | 3278 | 1.8 |
| 5 | 60 | 4585 | 2413 | 1.9 |

The average molecular weights of PVP-OH are reported in Table 1. It can be observed that the molecular weight decreases when the solvent/VP volume ratio increases.

Preparation of Block Copolymer PVP-PDLLA

The block copolymer was obtained by anionic ring-opening polymerization.

KH (0.567 g, 14 mmol) was placed in round-bottom flask 5 under an argon purge. Anhydrous THF was added via a double-tipped needle, the resulting dispersion was briefly stirred, and then the THF was removed. 30 mL of THF was added to the flask and the dispersion was cooled to 60° C. PVP-OH (1.5 g), previously dried in vacuum at 60° C. over $P_2O_5$ for 24 h, was solubilized in 30 mL of THF at 60° C. This solution was added to the stirred dispersion using a double-tipped needle, and resulting solution was maintained at 0° C. for 1 h. After warming to room temperature, the stirring was maintained for 4 h. The dispersion was transferred to another flask and 18-crown-6 (0.085 g, 0.32 mmol) was added at room temperature, and stirred for 30 min. The polymerization of D,L-lactide was initiated by quickly introducing D,L-lactide (1.5 g, 10 mmol) dissolved in 20 mL of THF. After 16 h, the polymerization was terminated by Several PVP-PDLLA block copolymers with variable compositions have been synthesized. As shown in Table 2, the average size of the micelle was between 44 and 168 nm, and the CAC was low. Sample 3a, with the shortest PLA segment, gave the highest CAC. The size distribution was however not unimodal, as revealed by SDP analysis (Table 3).

TABLE 3

Size Distribution of PVP-PDLLA micelles, SDP intensity analysis

| PVP-PDLLA Batch # | Water | | PBS | |
|---|---|---|---|---|
| | SDP Peak Amount | SDP Peak Mean (nm) | SDP Peak Amount | SDP Peak Mean (nm) |
| 1a | 85% | 62 ± 29 | 63% | 41 ± 13 |
| | 15% | 419 ± 133 | 34% | 290 ± 60 |
| 2a | 50% | 29 ± 6 | 56% | 124 ± 51 |
| | 50% | 199 ± 54 | 44% | 36 ± 12 |
| 3a | 60% | 106 ± 22 | 82% | 154 ± 69 |
| | 30% | 328 ± 111 | 18% | 38 ± 12 |
| 3b | 63% | 319 ± 46 | 96% | 243 ± 138 |
| | 37% | 100 ± 15 | 4% | 40 ± 13 |
| 3c | 69% | 129 ± 44 | 59% | 326 ± 59 |
| | 31% | 34 ± 7 | 41% | 78 ± 28 |
| 4a | 72% | 48 ± 26 | 52% | 37 ± 11 |
| | 28% | 158 ± 51 | 48% | 89 ± 21 |
| 4b | 64% | 39 ± 23 | 86% | 119 ± 37 |
| | 36% | 248 ± 88 | 14% | 26 ± 8 |
| 5a | 55% | 36 ± 10 | 62% | 106 ± 36 |
| | 45% | 109 ± 46 | 38% | 36 ± 11 |

As shown in Table 3, all samples gave micelles with a bimodal distribution, the size of the small particles was between 26 and 124 nm and the size of larger aggregates was between 106 and 419 nm.

To investigate drug entrapment efficiency, indomethacin was entrapped in PVP-PDLLA and PEG-PDLLA micelles as shown in Table 4.

TABLE 4

Incorporation of indomethacin in polymeric micelles.

| Initial Drug loading (%) | PEG-PDLA (63:37 wt %) | | PVP-PDLLA (60:-40 wt %) | |
|---|---|---|---|---|
| | Final drug loading (%) | Entrapment efficiency (%) | Final drug loading (%) | Entrapment efficiency (%) |
| 10 | 3 ± 1.0 | 30 ± 10 | 2 ± 0.5 | 20 ± 5 |
| 20 | 5 ± 1.2 | 25 ± 6 | 7 ± 3.1 | 35 ± 16 |
| 30 | 10 ± 0.9 | 33 ± 3 | 12 ± 1.8 | 40 ± 6 |
| 40 | 12 ± 1.2 | 30 ± 3 | 18 ± 1.2 | 45 ± 3 |
| 50 | 12 ± 1.0 | 24 ± 2 | 22 ± 2.0 | 44 ± 4 |

PEG-PDLLA (63:37 wt %) Mn = 7900, Mean diameter (unimodal analysis) = 110 ± 42 nm
PVP-PDLLA (60:40 wt %), Mn = 6600, Mean diameter (unimodal analysis) = 106 ± 45 nm
Data quoted are the mean of 3 measurements ± standard deviation The drug and the copolymer were dissolved in N,N-dimethylformamide (DMF) and dialyzed for 24 h, in the dark, against water. The solutions were filtered through a 0.22 µm pore-size filter and freeze-dried. Indomethacin loading was determined by measuring the UV absorbance of the micellar solution in DMF at 320 nm using a Hewlett Packard 8452A diode array spectrophotometer (Boise, ID).

The indomethacin entrapment efficiency in PVP-PDLLA and PEG-PDLLA micelles was similar at a low drug level. With increased drug loading, the entrapment efficiency of PVP-PDLLA micelles was superior to that of PEG-PDLLA micelles (considering copolymers having the same molecular weight). Without wishing to be bound by theory, it is believed that at low drug ratios the drug is first incorporated in the core and then, at higher ratios, it becomes incorporated into the PVP hydrophilic shell.

What is claimed is:

1. A micelle-forming composition, comprising:
   a hydrophobic core surrounded by a hydrophilic shell, wherein said hydrophilic shell is poly(N-vinyl-2-pyrrolidone); and
   a therapeutic agent, wherein said therapeutic agent is physically entrapped within said micelle.

2. The composition of claim 1, wherein the hydrophobic core is poly(D,L-lactic acid).

3. The composition of claim 1, wherein the hydrophobic core is selected from the group consisting of a polyester, a polyorthoester; a polyanhydride; a tyrosine derived pseudo-poly(amino acid); a polyphosphazene; a poly(alkylacrylate); a poly(β-benzyl-L-aspartate) and combinations thereof.

4. The composition of claim 3, wherein the polyester is selected from poly(glycolic acid), poly(lactic acid), poly(D-lactic acid), poly(D,L-lactic acid), lactide/glycolide copolymers, polycaprolactone and derivatives thereof.

5. The composition of claim 1, wherein the therapeutic agent is an antitumor compound.

6. The composition of claim 5, wherein the anti-tumor compound is selected from at least one phthalocyanine compound, anthracycline compound, antimetabolite, alkylating agent and taxane.

7. The composition of claim 6 wherein the phthalocyanine compound is aluminum chloride phthalocyanine.

8. The composition of claim 6 wherein the anthracycline compound is doxorubicin.

9. The composition of claim 6, wherein the antimetabolite is selected from methotrexate, mitomycin and 5-fluorouracil.

10. The composition of claim 6, wherein the alkylating agent is carmustine.

11. The composition of claim 6, wherein the taxane is paclitaxel.

12. The composition of claim 6, wherein the antimetabolite is selected from methotrexate, mitomycin and 5-fluorouracil.

13. The composition of claim 1, wherein the therapeutic agent is selected from a hydrophobic antibiotic, a hydrophobic antifungal agent, an immunomodulator, an antiviral drug and a steroidal or non-steroidal anti-inflammatory drug.

14. The composition of claim 1, wherein the therapeutic agent comprises a genome fragment.

15. A method for administering a therapeutic agent, comprising:
    providing a micelle-forming composition of claim 1, and
    administering the micelle-forming composition to a subject in need thereof.

* * * * *